(12) United States Patent
Ye et al.

(10) Patent No.: US 8,112,147 B2
(45) Date of Patent: Feb. 7, 2012

(54) METHOD AND APPARATUS FOR GENERATING DETERMINATION INDEXES FOR IDENTIFYING ECG INTERFERING SIGNALS

(75) Inventors: Wenyu Ye, Shenzhen (CN); Junbiao Hong, Shenzhen (CN); Yu Yue, Shenzhen (CN); Guanglei Zhang, Shenzhen (CN); Zehui Sun, Shenzhen (CN); Renqiang Zou, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 626 days.

(21) Appl. No.: 12/324,326

(22) Filed: Nov. 26, 2008

(65) Prior Publication Data

US 2009/0143693 A1    Jun. 4, 2009

(30) Foreign Application Priority Data

Dec. 4, 2007  (CN) .......................... 2007 1 0077572

(51) Int. Cl.
*A61B 5/04* (2006.01)
(52) U.S. Cl. ...................................................... 600/509

(58) Field of Classification Search .................. 600/508, 600/509, 513, 519
See application file for complete search history.

(56) References Cited

U.S. PATENT DOCUMENTS

2009/0124914 A1 *  5/2009  Kuo et al. ..................... 600/500

FOREIGN PATENT DOCUMENTS

| CN | 100998503 A | 7/2007 |
|---|---|---|
| WO | 2007029485 A1 | 3/2007 |

* cited by examiner

*Primary Examiner* — Brian T Gedeon
(74) *Attorney, Agent, or Firm* — Kory D. Christensen; Stoel Rives LLP

(57) ABSTRACT

A method for generating determination indexes for identifying ECG interfering signals includes acquiring ECG signals to obtain a sequence of data values representing original ECG signals; dividing the sequence of data values acquired during a period of time into groups and collecting all the minimum data values in their respective groups on a statistical basis; determining the minimum and the maximum data values in a minimum set made up of all the minimum data values in their respective groups; and using the difference between the minimum and the maximum data values as a first baseline drift determination index to identify at least one of low frequency interference and irregular interference.

17 Claims, 4 Drawing Sheets

METHOD AND APPARATUS FOR GENERATING DETERMINATION INDEXES FOR IDENTIFYING ECG INTERFERING SIGNALS

TECHNICAL FIELD

This disclosure relates to electrocardiogram (ECG) signal processing.

SUMMARY

A method and apparatus for generating determination indexes for identifying ECG interfering signals is disclosed.

DETAILED DESCRIPTION

Figure 1:
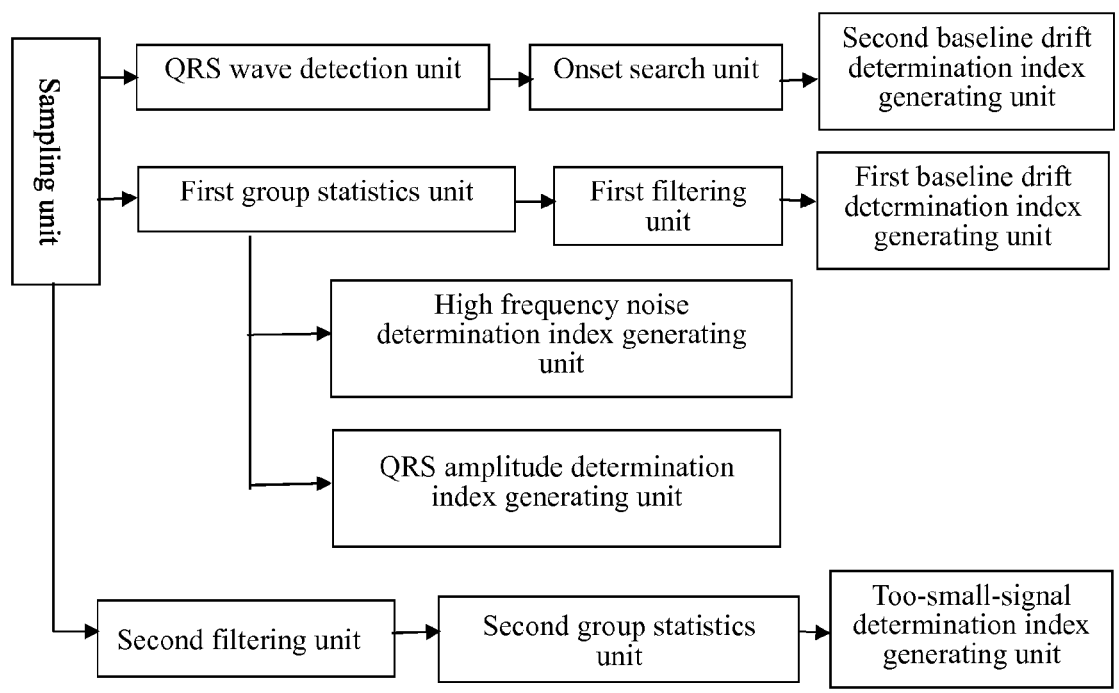
FIG. 1 a block diagram of an apparatus for generating determination indexes for identifying ECG signals.

ECG signals, as body surface manifestations of electrical changes taking place in the heart, are usually quite weak with an amplitude in the range of 10 μV~5 mV and a frequency in the range of 0.05~100 Hz. The measurement of ECG signals can be affected by various types of noise and interference:

(1) Baseline drift. Baseline drift can be caused by many factors including both human factors and instrumental factors. Examples of these factors include respiration, impedance between electrodes and human skin, disturbance caused by body movement, thermal noise from amplifiers, etc.

(2) High frequency interference from myoelectricity and electronic devices. Muscle contraction can generate a microvolt-level electric potential of about 50 ms, with an amplitude about 10% of the peak-to-peak ECG data value and a frequency ranging from 0 to 10 KHz. In addition, the high frequency current of surgical instruments may significantly distort the ECG signals, resulting in a high frequency noise ranging from 100 KHz~1 MHz, with an amplitude of about 200% of the peak-to-peak ECG data value, and a lasting time of 1 to 10 seconds.

(3) Electrode contact noise. This type of noise is an instantaneous interference caused by poor contact between electrodes and human skin or by detachment between the subject and the measuring system. Such a detachment, which can be continuous or discontinuous, might occur during movement and vibration. Electrode contact noise can be considered as a rapid baseline change that takes place randomly. Such a change may occur only once, producing only one step disturbance, or it may occur several times within a short period. This type of noise signal usually lasts for about 1 second, and its amplitude can be as great as the maximum output of an amplifier.

(4) Interference caused by the 50 Hz power frequency.

At present, there are two approaches to deal with the interference signals. The first approach centers on suppressing noise directly so as to improve the result of signal analysis. The second approach centers on effectively identifying the noise so as to select the best among multiple signal channels or to alarm correctly. Currently, the first approach has been more frequently implemented. Noise suppressing methods used include conventional filtering, curve fitting, self-adaptive processing, wavelet transformation, and the like, after which the signals are further analyzed. By contrast, the second approach receives less research effort, and the implementation of this approach usually involves using such methods as zero-crossing detection and variance calculation to obtain a rough estimation, which can only be adapted to a regular high frequency noise environment and depends upon stable and reliable detection of QRS waves.

The present disclosure provides a method for generating determination indexes for identifying ECG interfering signals. In one embodiment, the method includes a step A1 of acquiring ECG signals to obtain a sequence of data values representing original ECG signals. The method may also include a step B1 of dividing the sequence of data values acquired during a period of time into groups and collecting all the minimum data values in their respective groups on a statistical basis. In one embodiment, the method includes a step D1 of determining the minimum and the maximum data value in a minimum set made up of all the minimum data values in their respective groups. The method may further include a step E1 of using the difference between the minimum and the maximum determined in step D1 as a first baseline drift determination index, so as to identify at least one of low frequency interference and irregular interference.

In one embodiment, before step D1, the method includes a step C1 of filtering the minimum set made up of all the minimum data values in their respective groups.

The dividing in step B1 may be implemented in one of the following steps:

B11: dividing the sequence of data values into groups with a time window; and

B12: forming groups through sliding on the sequence of data values with a sliding time window.

In one embodiment, the period of time may be the last 2 seconds.

In an alternative embodiment, in step B1, the maximum in and the window height of each group are obtained on a statistical basis, the window height being defined as the maximum minus the minimum in a respective group.

After step B1, the following step may be further included: searching for the minimum window height within a period of time, and using the minimum window height as a high frequency noise determination index to identify high frequency noise.

In another alternative embodiment, after step B1, the following step may be further included: determining the maximum change among the window heights of all groups, and using the maximum change as a QRS amplitude determination index to identify the height of the QRS amplitude.

In still another alternative embodiment, after step A1 are further included the following steps:

A2: detecting QRS waves based on data of original ECG signals;

B2: determining the onset of each QRS wave;

C2: detecting fluctuation in a prior set of QRS onsets, the fluctuation being defined as the maximum minus the minimum in these QRS onsets, and using the fluctuation as a second baseline drift determination index to identify low frequency interference.

In still another embodiment, the method may further include the following steps after step A1:

A3: filtering data of the original ECG signals;

B3: dividing the filtered sequence of data values within a period of time into groups, detecting the maximum, minimum, and window height of each group on a statistical basis, wherein the window height being defined as the maximum minus the minimum in the group; and C3: determining the maximum window height within the last period of time, and using the maximum window height as a too-small-signal determination index to determine whether the signal is too small.

The present disclosure further provides an apparatus for generating determination indexes for identifying ECG interfering signals. In one embodiment, the apparatus includes a sampling unit for acquiring ECG signals to obtain a sequence of data values of original ECG signals. The apparatus may also include a first group statistics unit for dividing the sequence of data values into groups and collecting all the minimum data values in their respective groups on a statistical basis. The apparatus may further include a first baseline drift determination index generating unit for determining the minimum and the maximum from a minimum set made up of all the minimum data values in each group and using the difference between the minimum and the maximum as a first baseline drift determination index to identify low frequency interference and random interference. In one embodiment, the apparatus further comprises a first filtering unit for filtering the minimum set made up of all the minimum data values picked out in their respective groups.

In an alternative embodiment, the first group statistics unit is also used to detect, on a statistical basis, the maximum in, and the window height of, each group, the window height being defined as the maximum minus the minimum in respective group.

The apparatus may further comprise a high frequency noise determination index generating unit for detecting the minimum window height within a period of time and use the minimum window height as a high frequency noise determination index to identify the high frequency noise.

In another alternative embodiment, the apparatus further comprises a QRS amplitude determination index generating unit for searching for the maximum change among the window heights of all groups within a period of time and use the maximum change as a QRS amplitude determination index to identify the height of QRS amplitude.

In yet another alternative embodiment, the apparatus further comprises:
  a QRS wave detection unit for detecting QRS wave based on data of original ECG signals;
  an onset search unit for determining the onset of each QRS wave; and
  a second baseline drift determination index generating unit for detecting fluctuation in a last plurality of QRS waves and for using the fluctuation as a second baseline drift determination index to identify low frequency interference, the fluctuation being defined as the maximum minus the minimum among a plurality of QRS waves.

In still another alternative embodiment, the apparatus further comprises:
  a second filtering unit, for filtering data of original ECG signals;
  a second group statistics unit, for dividing the filtered sequence of data values within a period of time into groups, and collecting the maximum, minimum and window height on a statistical basis, wherein the window height in each group is defined as the maximum minus the minimum in the group; and
  a too-small-signal determination index generating unit, for determining the maximum window height within the last period of time, and using the maximum window height as a too-small-signal determination index to judge whether the signal is too small.

Referring now to FIG. 1, there is shown one embodiment of an apparatus for generating determination indexes for identifying ECG signals, in which a sampling unit, a first group statistics unit, a first filtering unit, and a first baseline drift determination index generating unit are coupled in sequence. The sampling unit is used for collecting ECG signals to obtain an original sequence of data values of ECG signals. The first group statistics unit is used for dividing a sequence of data values acquired during a period of time into groups and collecting the minimum, the maximum and the window height in respective groups on a statistical basis.

The first baseline drift determination index generating unit is used for determining the minimum and the maximum from a minimum set formed by all the minimum data values in respective groups, and the difference between the minimum and the maximum determined is used as the first baseline drift determination index to identify low frequency interference and irregular interference. A high frequency noise determination index generating unit, coupled with the first group statistics unit, is provided to determine the minimum window height change in a period of time, which is used as a high frequency noise determination index to identify high frequency noise.

A QRS amplitude determination index generating unit, also coupled with the first group statistics unit, is provided to determine the maximum window height change in a period of time, and use the maximum window height change as the QRS amplitude determination index. A QRS wave detection unit, coupled with the sampling unit, is provided to detect QRS waves based on original ECG signals. An onset search unit, coupled with the sampling unit, is provided to determine the onset of each QRS wave.

A second baseline drift determination index generating unit, coupled with the onset search unit, is provided to detect the onsets fluctuation in a prior set of QRS waves and employ the detected fluctuation as the determination index for a second baseline drift, so as to identify the low frequency interference. The fluctuation is defined as the result of the maximum onset in the plurality of QRS waves minus the minimum therein.

A second filtering unit, coupled with the sampling unit, is provided to filter the original ECG signal data. A second group statistics unit, coupled with the second filtering unit, is provided to divide the sequence of data values during a period of time after the filtering into groups and collect the maximum, the minimum and the window height on a statistical basis, wherein the window height of each group is defined as the maximum in the group minus the minimum therein. A too-small-signal determination index generating unit, coupled with the second group statistics unit, is provided to search for the maximum window height within a last period of time and employ the maximum window height as the too-small-signal determination index to determine whether the signals are too small.

Figure 2:
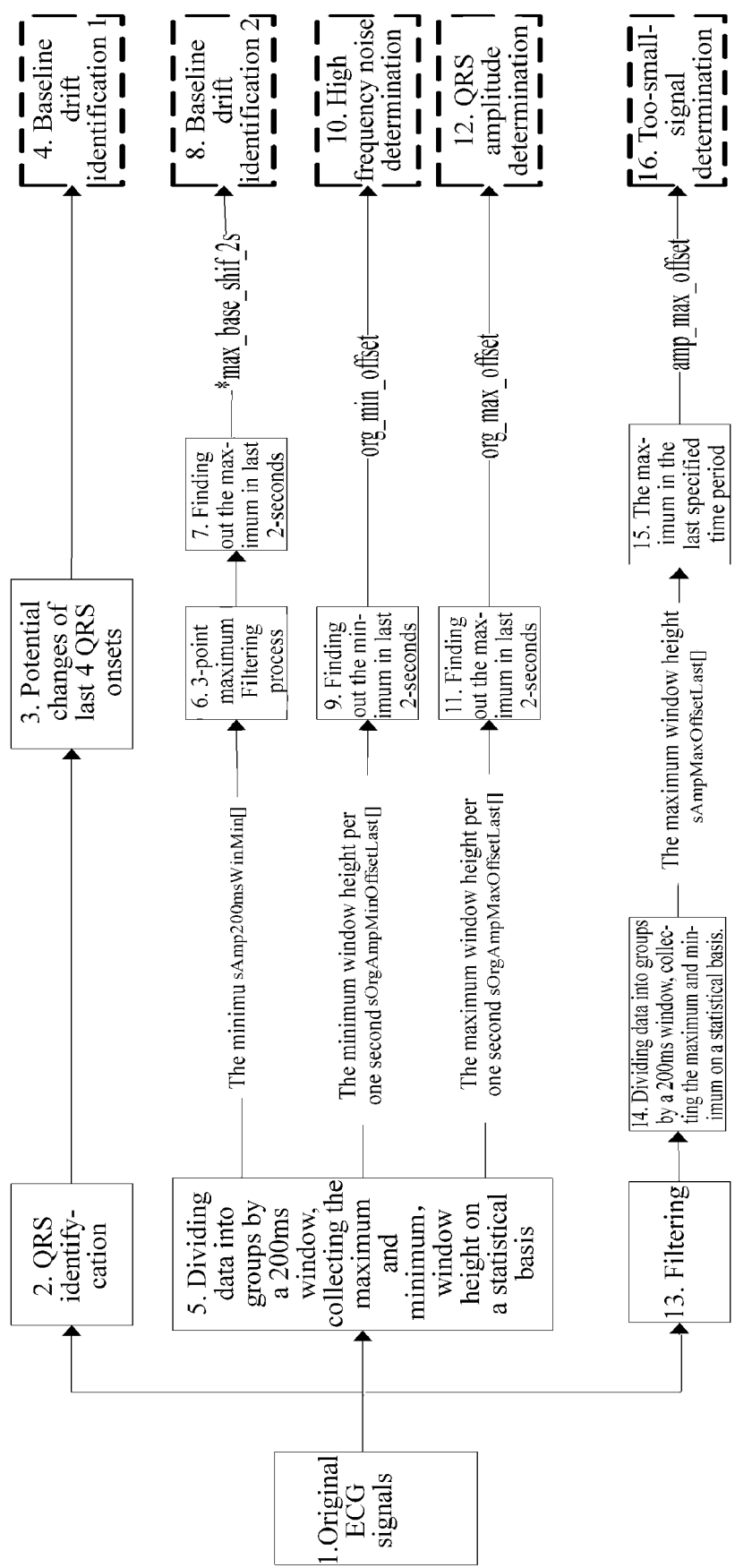
FIG. 2 is a flow chart of a method for generating determination indexes.

FIG. 2 is a flow chart illustrates a method of generating the determination indexes.

Step 1: Acquiring Original ECG Signals

Data may be acquired at a sampling rate of 250 Hz without any preprocessing step.

Step 2: Identifying QRS

After the band-pass filtering, differencing and integration of the original ECG signals, a local maximum may be detected in the integrated signals. When the local maximum exceeds the detection threshold, some characteristic parameters, such as the position of waves and the maximum slope are detected, and a judgment is made to see whether or not the waves conform to the determining conditions for QRS waves based on certain criterion. If yes, a QRS wave is detected and a parameter update is executed; if not, the current peak is considered as a noise peak. Since this QRS wave detection technique is a relatively mature one, its detailed description is omitted herein.

Step 3: Obtaining the Second Baseline Drift Determination Index

In one embodiment, one eighth (or other data values) of the maximum slope at the peak R detected in step 2 may be taken as a threshold, and the last point in the consecutive five (or other number) points detected some time (e.g., 200 ms, etc) before the peak R below the threshold is considered as the onset of a QRS wave. When a plurality (e.g., 4 or 5) such onsets have been detected, the maximum amplitude difference of the electrical levels of these onsets is selected as the second baseline drift determination index.

Step 4: Identifying the Baseline Drift

In this step, the level of low frequency interference is estimated by using the second baseline drift determination index obtained in step 3. If the ECG signals sampled fluctuate greatly in amplitude, it is considered that there is an intensive interference in the channel where the ECG signals were sampled. The second baseline drift determination index may be used in alarming or signal quality determination, depending on the actual application environment.

Step 5: Dividing Data into Groups

In one embodiment, data within a period of time of time is divided by using a time window (e.g., 100 ms~1 s). The maximums and the minimum data values in respective windows are collected on a statistical basis, and then the respective window heights are calculated. In one embodiment, the specified time period can be the last 2 or 3 seconds, and in the following embodiment, the 2 seconds period is used for illustration.

Since in a filtering process some irregular interference is likely to be treated as QRS waves, it is the original ECG signals that are divided into windows in this step. Considering that the QRS duration ranges from 40 ms to 120 ms, if a window of 200 ms is used to divide data sampled during the last 2 second period, 10 maximums and minimum data values can be collected respectively on a statistical basis, and a window height can be calculated by subtracting the minimum from the corresponding maximum.

Step 6: Filtering

In one embodiment, the minimum data values sAmp200 msWinMin□ in respective windows are filtered consecutively with a so called 3-point maximum filtering.

Step 7: Finding the Maximum and Minimum,

After the filtering process in step 6. the maximum and the minimum among the minimum data values of respective windows are determined.

Step 8: Obtaining the First Baseline Drift Determination Index

The amplitude change, or the difference between the maximum and the minimum determined in step 7. may be used as the first baseline drift determination index. With this determination index, a baseline drift with its width greater than 200 ms~400 ms can be detected, since the 3-point maximum filtering deals with the minimum data values of respective windows during a period of time. Therefore, any baseline drifts with their durations longer than 200 ms~400 ms can be detected. The baseline drift detection is basically synchronized with QRS detection, although there is a delay of 400 ms. The first baseline drift determination index can also be used to determine the intensity of irregular interference, because the difference between the maximum and the minimum corresponds to the intensity. The first baseline drift determination index may be used in alarming or signal quality determination, depending on the actual application environment.

Step 9: Determining the Minimum Window Height in the Last 2-Second Period

The minimum window height within the last 2 seconds can reflect the situation of high frequency noise, because the amplitudes of the high frequency noise are less than those of QRS waves. First, if the minimum window height in one second is collected, there are 2 minimum window heights within the last 2 seconds. In the multi-lead ECG analysis, however, multiple channels exist, so all the minimum window heights are stored in a two-dimensional array sOrgAmpMinOffsetLast□. Then, the minimum in window heights org_min_offset in the last 2-second period may be searched for and the minimum determined is used as a high frequency noise determination index.

Step 10: Determining the High Frequency Noise

In one embodiment, the high frequency noise determination index obtained in step 9 is used to determine the intensity of high frequency interference. This determination index can be used in combination with other determination indexes of the present disclosure to determine the signal quality for alarming or selecting the preferred signals. Since the amplitudes of high frequency noise are less than those of QRS waves, the minimum window height in the last 2-second period can reflect the intensity of high frequency noise. If two channels of signals are available, this data value can be used as a determination index for comparing the signal qualities of these two channels.

Step 11: Searching for the Maximum Window Height in the Last 2-Second Period

Similar to the principles of step 9. the maximum window height in the last 2-second period can reflect the amplitude of the QRS complex. In one embodiment, all the maximum window heights are stored in a two-dimensional array sOrgAmpMaxOffsetLast□. Then, the maximum in window heights org_max_offset in the last 2-second period is searched for, which reflects the amplitude of the QRS complex. The maximum window height in the last 2-second period is used as a QRS amplitude determination index.

Step 12: Determining the Amplitude of QRS Complex

The QRS amplitude determination index obtained in step 11 can reflect the amplitude height of the QRS complex and can therefore be used for lead optimization in multi-channel ECG analysis. In multi-lead optimization, the lead is selected, which provides relatively large and physiologically-reasonable amplitude of the QRS complex. Actually, the QRS amplitude determination index is likely to be affected by step-like interference and therefore may be used in combination with the first baseline drift determination index to determine an effective signal amplitude. When the baseline drift identification determination index 2 is close to the QRS amplitude determination index, which indicates that the QRS amplitude determination index is likely to have been generated under the influence of the baseline drift identification determination index, such kind of leads should be avoided in the optimization. Therefore, the QRS amplitude determination index can be used for alarming or ECG lead optimization, depending on the application environments.

Step 13: Filtering

In this step, the original ECG signals are filtered, in one embodiment, to suppress high and low frequency noise interference preliminarily. The filtering techniques used in the present disclosure can be the simple integral coefficients band-pass filtering method or other methods which are familiar to skilled artisans.

Step 14: Grouping and Counting the Maximums and the Minimum Data Values

In one embodiment, the data filtered in step 13 are divided into groups by a time window of 200 ms, and the maximum and minimum in each group are collected on a statistical basis. After band-pass filtering, the original ECG signals are divided into groups by time windows of 200 ms. The maximums and minimum data values in respective windows are collected on a statistical basis and respective window heights are calculated. All the maximum window heights in one second may be stored in the array sAmpMaxOffsetLast[].

Step 15: Searching for the Maximum in the Last Specified Time Period

The maximum window height within a last period of time (for example, within a user period of time for detecting asystole) is searched for. The maximum window height is used as the determination index for too-small signal amplitude.

Step 16: Determining Too-Small Signals

A too-small-signal determination index is used in this step, wherein a signal is considered lost when the amplitude of the signal after being filtered is less than a specified threshold within a specified time period for asystole detection. The too-small-signal determination index is used for determining whether it is possible to use current signals for valid analysis. Due to the fact that noise has been removed, the signals are more likely to indicate the authentic QRS amplitude, and can therefore be used as a preferred reference for subsequent determination.

This step differs from step 12 in that it is used for determining signal amplitude for a relatively long time period so as to reliably determine whether a channel is valid. If multiple leads are used to detect ECG signals, signals in respective leads are analyzed through above steps to obtain, in one embodiment, five data values representing respective signal qualities. The five data values are compared to select, if possible, an optimum lead, which has relatively high amplitude, low level of high frequency noise and baseline drift, to be used in signal processing such as heart rate calculation, ARR analysis, and the like. If no optimum lead is available, a sub-optimum lead can be picked out for analysis, by comparing their QRS amplitudes and high frequency noise components and baseline drifts.

In one embodiment, the time windows in step 5 and step 14 may be replaced with a sliding time window, which slides over a sequence of data values of ECG signals at a specified interval, to obtain several groups of data. Thereafter, the maximum and minimum in respective groups are determined.

Owing to the removal of abrupt waveforms within a width of 200 ms based on the characteristics of ECG signals, the determination indexes of the present disclosure can effectively identify low frequency interference, irregular interference which are clinically common, high frequency interference, and other signals, while providing information on QRS amplitudes of respective channels. The multi-lead optimization analysis depends on a judgment by incorporating above-described determination indexes.

The operations in the present disclosure include merely addition, subtraction and comparison, which are relatively simple and require few system resources, therefore the present disclosure can easily find applications in such instruments as ECG detectors based on embedded microprocessor.

Figure 3:
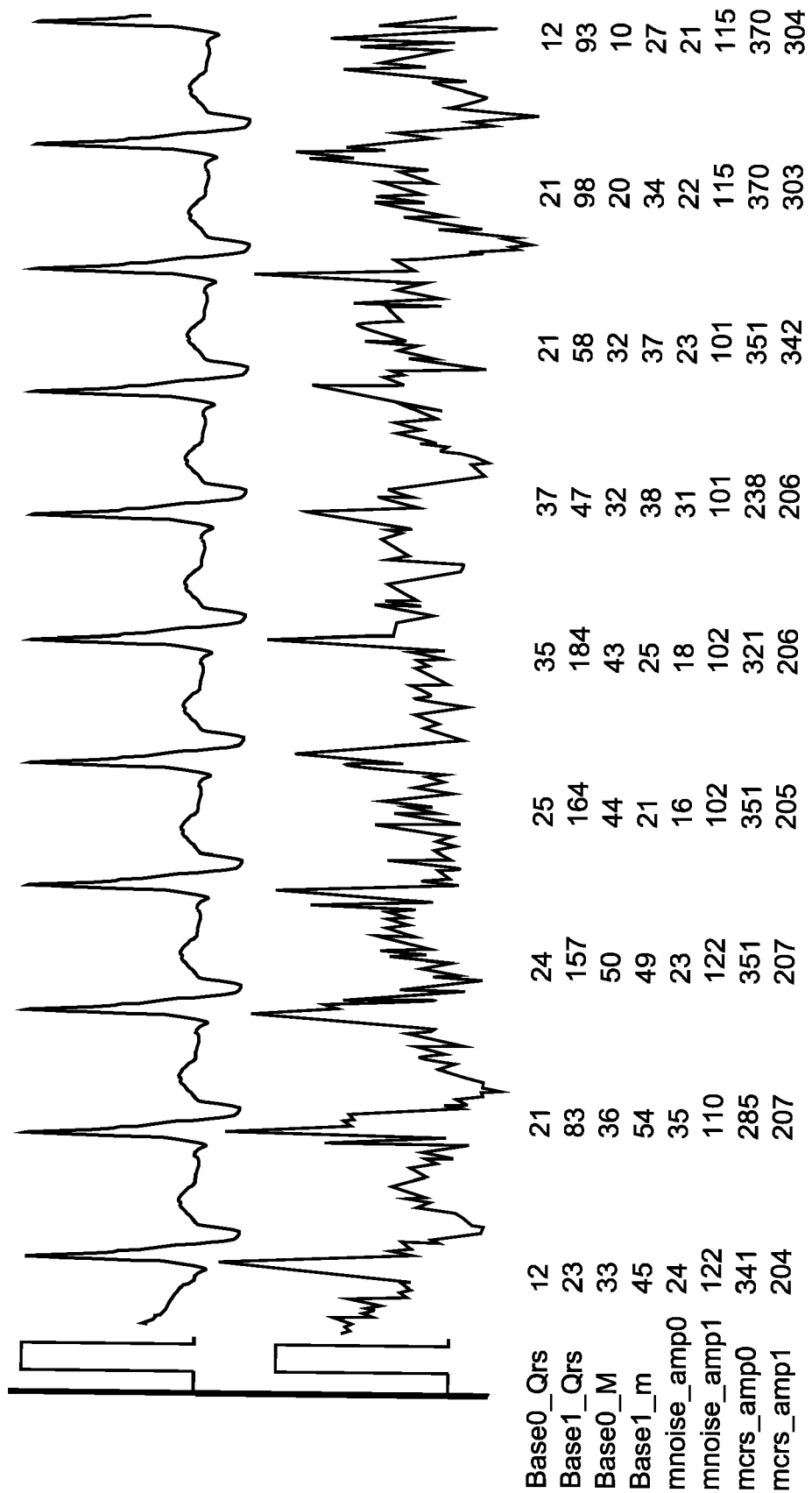
FIG. 3 is a graph showing analysis results of an ECG containing high frequency noise.
Figure 4:
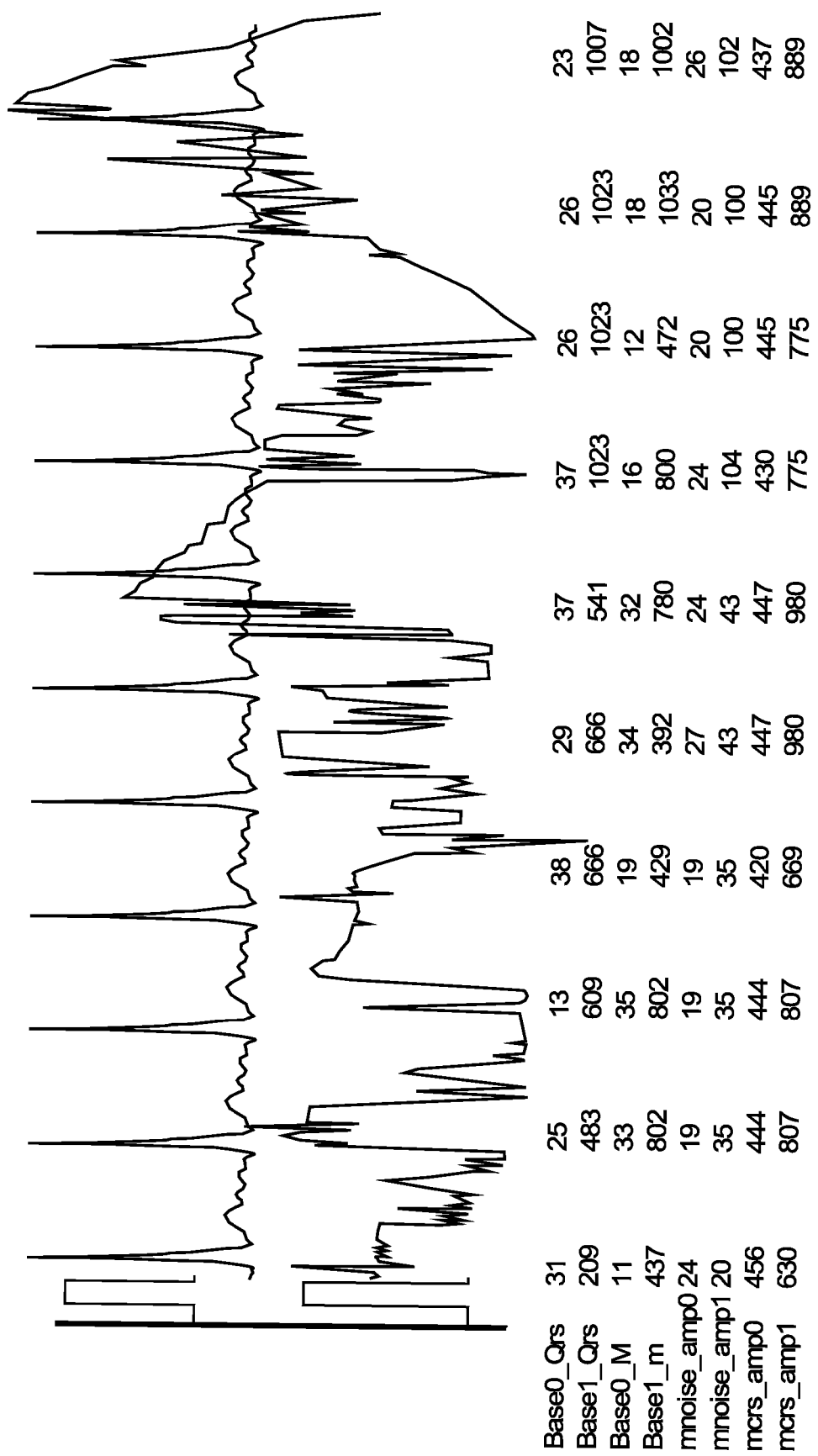
FIG. 4 is a graph showing analysis results of an ECG containing baseline drift.

FIG. 3 and FIG. 4 show index analysis results actually detected respectively with high frequency noise and baseline drift existed in 2-channel ECG signals. In these two figures, Base_Qrs corresponds to the second baseline drift determination index, which is based on the level of QRS onset potential change; Base_M corresponds to the first baseline drift determination index, which is the maximum in the last 2 s time window obtained after a continuous 3-point maximum filtering process; mnoise_amp represents the minimum in the last-2-second window, or the high frequency noise determination index; and mqrs_amp corresponds to the maximum in the last-2-second window, which can be used as the QRS amplitude determination index.

It can be seen from FIG. 3 that the mnoise_amp of Channel 1 is obvious higher than that of Channel 0. This suggests an existence of high frequency noise in Channel 1. In Channel 1 of FIG. 4 there exists low frequency interference and irregular interference. We can determine by studying the indexes Base_Qrs and Base_M that the data values of Channel 1 are obviously higher than those of Channel 0 and can determine thereby that a baseline drift exists in Channel 1. With the results of the indexes analysis, a program can provide a corresponding prompt as required, or perform an optimization of multiple signals to improve the reliability of analysis results.

The present invention has been described in detail with reference to various embodiments, but such description should not be interpreted as limiting the scope of the invention. It is to be understood that various changes and substitutions can be made by a skilled artisan without departing from the scope of the invention.

What is claimed is:

1. A method for generating determination indexes for identifying ECG interfering signals, comprising:
   A1: acquiring ECG signals to obtain a sequence of data values representing original ECG signals;
   B1: dividing the sequence of data values acquired during a period of time into groups and collecting all the minimum data values in their respective groups on a statistical basis;
   D1: determining the minimum and the maximum data values in a minimum set made up of all the minimum data values in their respective groups; and
   E1: using the difference between the minimum and the maximum data values determined in step D1 as a first baseline drift determination index to identify at least one of low frequency interference and irregular interference.

2. The method of claim 1, wherein, before step D1, the method includes:
   C1: filtering the minimum set made up of all the minimum data values in their respective groups.

3. The method of claim 1, wherein the dividing in step B1 is implemented in one of the following steps:
   B11: dividing the sequence of data values into groups by a time window; and
   B12: forming groups through sliding on the sequence of data values with a sliding time window.

4. The method of claim 1, wherein the period of time is the last 2 seconds.

5. The method of claim 1, wherein, in step B1, the maximum in, and the window height of, each group are further obtained on a statistical basis, the window height being defined as the maximum minus the minimum in a respective group.

6. The method of claim 5, wherein, after step B1, the method further includes:
   searching for the minimum window height within a period of time, the minimum window height being used as a high frequency noise determination index to identify high frequency noise.

7. The method of claim 6, wherein, after step B1, the method further includes:
    searching for a maximum change among the window heights of all groups, the maximum change being used as a QRS amplitude determination index to identify the height of a QRS amplitude.

8. The method of claim 1, wherein, after step A1, the method further includes:
    A2: detecting a QRS wave based on data of the original ECG signals;
    B2: searching for the onset of each QRS wave; and
    C2: detecting a fluctuation in a last plurality of QRS waves, the fluctuation being defined as the maximum minus the minimum in a plurality of QRS onsets, and using the fluctuation as a second baseline drift determination index to identify low frequency interference.

9. The method of claim 1, wherein, after step A1, the method further includes:
    A3: filtering data values representing original ECG signals;
    B3: dividing the filtered sequence of data values within a period of time into groups, obtaining the maximum, minimum, and window height on a statistical basis, wherein the window height in each group being defined as the maximum minus the minimum in the group; and
    C3: searching for the maximum window height within the last period of time, and using the maximum window height as a too-small-signal determination index to determine whether the signal is too small.

10. An apparatus for generating determination indexes for identifying ECG interfering signals, comprising:
    a sampling unit for acquiring ECG signals to obtain a sequence of data values representing original ECG signals;
    a first group statistics unit for dividing the sequence of data acquired during a period of time into groups and for collecting all the minimum data values in their respective groups on a statistical basis; and
    a first baseline drift determination index generating unit for determining the minimum and the maximum data values from a minimum set made up of all the minimum data values in each group and using the difference between the minimum and the maximum data values as a first baseline drift determination index to identify at least one of low frequency interference and random interference.

11. The apparatus of claim 10, further comprising a first filtering unit for filtering the minimum set made up of all the minimum data values picked out in their respective groups.

12. The apparatus of claim 11, wherein the first group statistics unit is also used to obtain on a statistical basis the maximum in, and the window height of, each group, the window height being defined as the maximum minus the minimum in respective group.

13. The apparatus of claim 12, further comprising a high frequency noise determination index generating unit for detecting the minimum window height within a period of time, and using the minimum window height as a high frequency noise determination index to identify high frequency noise.

14. The apparatus of claim 13, further comprising a QRS amplitude determination index generating unit for searching for the maximum change among the window heights of all groups within a period of time, and using the maximum change as a QRS amplitude determination index to identify the height of the QRS amplitude.

15. The apparatus of claim 10, further comprising:
    a QRS wave detection unit for detecting a QRS wave based on data values representing the original ECG signals;
    an onset search unit for determining the onset of each QRS wave; and
    a second baseline drift determination index generating unit for detecting fluctuation in a last plurality of QRS waves, and using the fluctuation as a second baseline drift determination index to identify low frequency interference, the fluctuation being defined as the maximum minus the minimum among a plurality of QRS waves.

16. The apparatus of claim 10, further comprising:
    a second filtering unit for filtering data values representing the original ECG signals;
    a second group statistics unit for dividing the filtered sequence of data values within a period of time into groups, and collecting the maximum, minimum, and window height on a statistical basis, the window height in each group being defined as the maximum minus the minimum in the group; and
    a too-small-signal determination index generating unit for determining the maximum window height within the last period of time, and using the maximum window height as a too-small-signal determination index to judge whether a signal is too small.

17. An apparatus for generating determination indexes for identifying ECG interfering signals, comprising:
    means for acquiring ECG signals to obtain a sequence of data values representing original ECG signals;
    means for dividing the sequence of data values acquired during a period of time into groups and collecting all the minimum data values in their respective groups on a statistical basis;
    means for determining the minimum and the maximum data values in a minimum set made up of all the minimum data values in their respective groups; and
    means for using the difference between the minimum and the maximum data values as a first baseline drift determination index to identify at least one of low frequency interference and irregular interference.

* * * * *